United States Patent
Ichihashi

(10) Patent No.: US 7,442,549 B2
(45) Date of Patent: Oct. 28, 2008

(54) METHOD OF CONSTRUCTING ORCHID HAPLOID BY TREATING UNFERTILIZED ORCHID FLOWER WITH AUXIN AND METHOD OF GROWING ORCHID

(75) Inventor: Syoichi Ichihashi, Kariya (JP)

(73) Assignee: Sapporo Breweries Limited, Tokyo (JP)

( * ) Notice: Subject to any disclaimer, the term of this patent is extended or adjusted under 35 U.S.C. 154(b) by 471 days.

(21) Appl. No.: 10/521,794

(22) PCT Filed: Jul. 10, 2003

(86) PCT No.: PCT/JP03/08799

§ 371 (c)(1),
(2), (4) Date: Jan. 21, 2005

(87) PCT Pub. No.: WO2004/008842

PCT Pub. Date: Jan. 29, 2004

(65) Prior Publication Data

US 2005/0289663 A1 Dec. 29, 2005

(30) Foreign Application Priority Data

Jul. 23, 2002 (JP) ............................. 2002-213746

(51) Int. Cl.
C12N 5/00 (2006.01)
C12N 5/02 (2006.01)
A01H 9/00 (2006.01)
A01H 11/00 (2006.01)
A01H 5/00 (2006.01)

(52) U.S. Cl. ................... 435/430.1; 435/430; 435/420; 800/295; 800/298; 800/299

(58) Field of Classification Search .............. 435/430.1, 435/430, 420; 800/295, 298, 299
See application file for complete search history.

(56) References Cited

FOREIGN PATENT DOCUMENTS

JP 2000-342093 12/2000

OTHER PUBLICATIONS

Xian Sheng Zhang and Sharman D. O'Neill, Ovary and Gametophyte Development Are Coordinately Regulated by Auxin and Ethylene following Pollination, The Plant Cell, vol. 5, pp. 403-418, Apr. 1993.*

Campion, B. et al., Spontaneous and induced chromosome doubling in gynogenic lines of onlon (*Allium cepa L.*), Plant Breed, vol. 114, No. 3, pp. 243-246, 1995.

Kobayashi, Hitoshi. "New Plant Breeding Technology", Yokendo, pp. 110-112 1987.

Kuraishi, Shin. "Plant Hormone", second version, Tokyo University Shuppannkai, pp. 45-46 1998.

(Continued)

*Primary Examiner*—Kent Bell
(74) *Attorney, Agent, or Firm*—Oblon, Spivak, McClelland, Maier & Neustadt, P.C.

(57) ABSTRACT

It is intended to provide a pure line plant which is required in constructing a seed propagation variety of orchid. An auxin solution is dropped to unfertilized orchid flowers so as to form seeds based on parthenogenesis. Then these seeds are germinated and haploid plants are selected from orchid plants thus grown. The germinating seeds judges as haploid plants are grown to give pure line plants having doubled chromosomes. Thus, a seed propagation variety of orchid is obtained.

7 Claims, 3 Drawing Sheets

OTHER PUBLICATIONS

Ito, Itsuhiko et al. "Calanthe and its Group", Seibundo-Sinkosha, pp. 206-207 1969.

Mori, Genjiro et al. "Studies on the Possibility of Including Apomixis in Some Orchids", The magazine of horticulture society, second additional version of vol. 58 1989.

Mori, Genjiro et al. "Seed formation of Zygopetalum Mackayi by Apomixis", The magazine of horticulture society, second additional version of vol. 60, pp. 466-467 1991.

Uchida, Kazuhito. "Tropical Orchid the Orchid", Kodansha, 99 1982.

Yoshiaki Kitani, "Induction of Parthenogenetic Haploid Plants With Brassinolide", Japanese Journal of Genetics, XP-002400720, vol. 69, No. 1, 1994, pp. 35-39.

Anhthu Q. Bui, et al. "Three 1-Aminocyclopropane-1-Carboxylate Synthase Genes Regulated by Primary and Secondary Pollination Signals in Orchid Flowers", Plant Physiology, XP-002400721, vol. 116, No. 1, Jan. 1998, pp. 419-428.

Michael S. Strauss, et al. "Postpollination Phenomena in Orchid Flowers. X. Transport and Fate of Auxin", Botanical Gazette, XP-008057797, vol. 143, No. 3, 1982, pp. 286-293.

Joseph Arditti, et al. "The Effects of Auxin, Actinomycin D., Ethionine, and Puromycin on Post-Pollination Behavior by Cymbidium (ORCHIDACEAE) Flowers", American Journal of Botany, Botanical Society of America, XP-008057821, vol. 56, No. 6, 1969, pp. 620-628.

* cited by examiner

OBSERVATION RESULTS OF CHROMOSOMES

PLANTS ORIGINATING IN SELF-POLLINATION 2n=32 (ROOT APEX)

PLANTS ORIGINATING IN NAA TREATMENT n=16 (ROOT APEX)

METHOD OF CONSTRUCTING ORCHID HAPLOID BY TREATING UNFERTILIZED ORCHID FLOWER WITH AUXIN AND METHOD OF GROWING ORCHID

BACKGROUND OF THE INVENTION

1. Field of the Invention

This invention generally relates to a method of constructing orchid haploid by treating unfertilized orchid flower with auxin.

2. Description of the Related Art

Orchid is always very popular as a flower for enjoyment, in recent years, and a mass cultivation is performed in order to meet the demand for supply. As a popular reason, in accordance with a consumer's taste, a variety of orchid with sufficient economical efficiency which can be tolerated to the mass cultivation have been developed. These varieties of orchid have been developed by traditional cross-breeding. This cross-breeding means selecting any superior individuals from a seedling group which was obtained by mating. The obtained superior individuals need to propagate to a level suitable for mass consumption, and a cloning by tissue cultures is used as a mass propagating method.

The technology of the cloning by tissue cultures is still unstable, and has problems, such as difficulty depending on the varieties of orchid, and any mutation in tissue cultures. In order to avoid these problems, solutions which suppresses a proliferation rate of cloning which performs experimental proliferation of cloning for every each varieties of orchid is used. However, neither of the ways can suppress a generating of mutation completely, but a generation of any malformated flower is found in orchid of the proliferation of cloning by tissue cultures.

This mutation is caused by the cell proliferation which is not considered in natural circumstances where it is performed in a stage of tissue culturing. By contrast, there is very little generating of mutation in the division method by natural proliferation of plants performed in the past. However, it is difficult for the proliferation rate to be suppressed with very low rate and to cope with mass consumption in recent years by the division of plants.

Although propagation that there are no mutational problem and that the high rate of proliferation is obtained by generally using seeds for propagation is performed, since orchid plants have high hybridization rate, the homogeneity in a seed propagation group has a notable problem. Thus, there is a method using haploid plants as one way of improving the homogeneity in this seed propagation group.

As for haploid plants, it is possible to have a doubled gene by colchicines treatment. Plants having a doubled gene are pure line plants and a uniform seed propagation group is obtained by performing self-mating of these pure line plants. Furthermore, there is no hereditary difference between individuals in the first hybrid (F1 plant) obtained by mating between pure line plants, it is possible to obtain uniform future generations, and the uniform seed propagation group can be also generated from this F1 hybrid.

Since these seed propagation groups are not only uniform, but also there is little risk of mutation due to not performing the proliferation of cloning by tissue cultures, and the desirable additional characteristics, such as heterosis, are also expected in seed propagation groups obtained from the F1 hybrid. As for the proliferation of cloning by tissue cultures, since a culturing period will become long when mass proliferation is performed from the same tissue cultures, although the risk of mutation also becomes high, mass propagation is achieved in a seed propagation group for a short period of time.

As for the method of constructing haploid, although it is effective only in a specific plant, generally, an anther culture method and an interspecies crossing method are established. Although the method of constructing haploid using the anther culture method is available for breeding tobacco, rice and wheat, and the method of constructing haploid using the interspecies crossing method is available for breeding potatoes, barley (Hitoshi Kobayashi, 1987, "*New plant breeding technology*", Yokendo, pp. 110-112), it has not been recognized that the method of constructing haploid is applied to the variety of orchid.

On the other hand, auxin is one of the plant growth regulators (plant hormone), one of the action has fruit bearing without pollination and hypertrophy growth of fruits. It is found that when plants are treated with auxin, even if not fertilized, fruits will occur parthenogenesis which take places hypertrophy growth, and will continue to grow (Shin Kuraishi, 1988, "*plant hormone*", second version, Tokyo University Shuppannkai, pp. 45-46). This action is applied to a culture of tomato, even if pollination is not performed, set of fruits and hypertrophy are performed with auxin to an unfertilized flower of tomato. This is because of the action of auxin, the parthenogenesis is induced and an unfertilized ovary grows. However, the high concentrated auxin will induce a generation of ethylene and make fruits fall off plants, thus unless it is moderate concentration of auxin, an unfertilized ovary will fall, then seeds cannot be obtained.

When pollens of calanthes and cymbidiums are mated to *Bletilla striata* which is one variety of orchid, many seeds will be obtained easily. However, when these seeds are planted, judging from its germination and a feature of its seedling, the possibility of parthenogenesis is very high. This would be due to ploidy parthenogenesis of egg cell from which the ovary developed by stimulus of pollens hormone or forming seeds by apogamy in which embryo originates from nutritional tissues of mother's bodies, such as placenta (Itsuhiko Ito, Koji Karasawa, 1969, "*Calanthe and its group*", Seibundo-sinkosha, pp. 296-207).

Moreover, it is reported that parthenogenesis has been induced by giving naphthaleneacetic acid which is one kind of auxin to stigma of Zygopetalum which is one variety of orchid (Genjiro Mori, Koichi Yamaoka, Hideo Imanishi, 1989, "*Studies on the possibility of including apomixis in some orchids*", The magazine of horticulture society, second additional version of volume 58; Genjiro Mori, Koichi Yamaoka, Hideo Imanishi, 1991, "*Seed formation of Zygopetalum mackayi by apomixis*", The magazine of horticulture society, second additional version of volume 60, pp. 466-467).

SUMMARY OF THE INVENTION

It is a general object of the present invention to provide haploid plants and pure line plants from seeds which auxin is applied to unfertilized orchid flowers so as to form seeds based on parthenogenesis.

In order to achieve the above-mentioned object, there is provided according to one aspect of the present invention a method of constructing orchid haploid, wherein an auxin solution is dropped to unfertilized orchid flowers so as to form seeds based on parthenogenesis, then these seeds are germinated and grown so as to obtain orchid haploid.

Additionally, in the method of constructing orchid haploid according to the present invention, the dropping of the auxin solution to unfertilized orchid flowers is treated within 30 days after blooming.

Additionally, in the method of constructing orchid haploid according to the present invention, the auxin solution is dropped to a column or a part including the column of unfertilized orchid flowers.

Additionally, in the method of constructing orchid haploid according to the present invention, a concentration of the auxin solution is between 0.1 and 5.0%.

Additionally, in the method of constructing orchid haploid according to the present invention, the auxin solution is selected from a group consisting of Indoleacetic acid (IAA), 4-chloro-indoleacetic acid, phenylacetic acid, 2,4-dichloro-phenoxyacetic acid (2,4-D), α-naphthaleneacetic acid (NAA), 2,6-dichloro-benzoic acid, indolebutyric acid (IBA), 4-chloro-phenoxyacetic acid, 5-chloro-indazole ethyl acetate and 2,4,5-trichloro-phenylacetic acid.

In order to achieve the above-mentioned object, there is also provided according to another aspect of the present invention, a method of constructing a seed propagation variety of orchid, wherein an auxin solution is dropped to unfertilized orchid flowers so as to form seeds based on parthenogenesis, and these seeds are germinated and haploid plants are selected from orchid plants thus grown, and the germinating seeds judges as haploid plants are grown to give the seed propagation variety of orchid.

Additionally, in the method of constructing a seed propagation variety of orchid according to the present invention, the judgement as haploid plants are done by measuring DNA contents or the number of chromosomes of samples obtained within a period between one month and five months after germination.

According to the present invention, the growing orchid haploid to provide a pure line plant which is required in constructing a seed propagation variety of orchid can be provided. Thus, a stable supply of superior breed with low risks like mutations is possible for a long period of time.

Other objects, features and advantages of the present invention will become more apparent from the following detailed description when read in conjunction with the accompanying drawings.

DESCRIPTION OF THE PREFERRED EMBODIMENTS

A description will now be given, with reference to the embodiments and drawings according to the present invention.

First, in order to achieve a seed formation with an unfertilized flower, a treatment with auxin is done. It is appropriate to treat with auxin within 30 days after a bloom day.

Figure 1:
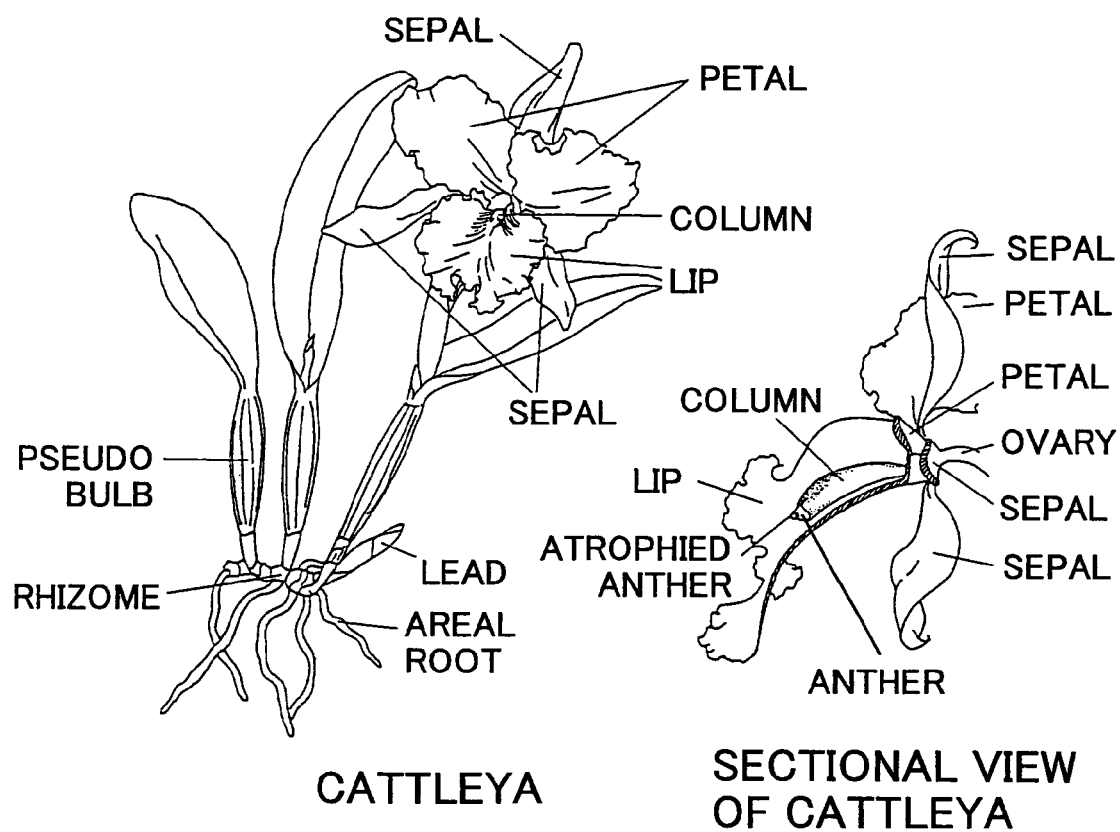
FIG. 1 is views showing general form of orchid flowers.

As a treated part, column or a part including column is treated by auxin solution by spraying, coating or dropping. FIG. 1 is views showing general form of orchid flowers (Kazuhito Uchida, 1982, "*Tropical Orchid The Orchid*", Kodansha, 99).

In order to prevent the solution falling by gravity because of facing downward of flowers depending on kind of varieties and blooming situation of orchid, it is also effective in the treating part to stagnate auxin by mixing agar, starch, etc. in the solution and improving viscosity by heating or by making lanolin suspension and forming a paste.

A concentration of auxin solution is between 0.1 and 5.0%.

Indoleacetic acid (IAA), 4-chloro-indoleacetic acid, phenylacetic acid, 2,4-dichloro-phenoxyacetic acid (2,4-D), α-naphthaleneacetic acid (NAA), 2,6-dichloro-benzoic acid, indolebutyric acid (IBA), 4-chloro-phenoxyacetic acid, 5-chloro-indazole ethyl acetate, 2,4,5-trichloro-phenylacetic acid can be used as auxin.

A withering of perianth is observed immediately after the treatment, and hypertrophy of ovary will be found in about one week.

Although the growth of ovary and the seed formation differ from depending on kind of varieties of orchid, set of seeds is observed from two to six months after treatment. In the meantime, it fully needs to be cautious of fall off seeds. Also, compared with the usual mating and fruition, seeds may ripen a little early about one to two months.

The ripen seeds are obtained and these seeds are planted by the germfree condition. The planting is performed according to the conventional method. The rate of germination of seeds becomes low compared with the usual mating of seeds.

If germination is observed and these buds grow in regular sizes, it will affirm promptly whether they are haploid plants. The check of being haploid plants takes out some tissues of root tips, measures the number of chromosomes or amounts of DNA contents, and is performed by comparing these values with plants originating in self-pollination. Because the number of the chromosomes of haploid plants may have doubled naturally after passing a regular period after germination, it is necessary to perform the check of haploid plants within one to five months after germination.

Hereafter, one embodiment is explained as a preferred embodiment of the invention.

First Embodiment

In the first embodiment, Bletilla. Brigantes "H5-11" was used. The supplied testing plants were grown in the conventional method. The blooming was affirmed, pollens were removed and a treatment of dropping of 10 micro liter was performed with the warmed lanolin paste which contains 2% of α-naphthaleneacetic acid at column using the syringe. Since two or more flowers might exist in the same inflorescence, the above-mentioned treatment was performed about for each one repeatedly five or more times.

After individuals in which its ovary got fat are ripened completely (6 to 7 months after the treatment), then they were obtained, they were sterilized their surface for 5 minutes with 0.5% of sodium hydrochlorite solution, planted them on a medium in germfree container, and the germination was forced.

After planting, when the number of planted seeds and the number of seed with embryo were observed, 11 seeds with embryo were observed out of 7000 of the planted total number of seeds.

The composition of a culture medium used for planting of seeds is shown in Table 1.

TABLE 1

THE INGREDIENT TABLE OF THE CULTURE MEDIUM
USED BY STERILE SEEDS PLANTING IN THE EMBODIMENT

| | |
|---|---|
| HYPONEX (6.5:6.0:19.0) | 3 g/l |
| SACCHAROSE | 20 g/l |
| AGAR | 10 g/l |

2 weeks after planting of seeds, 8 buds of plants originating in auxin treatment were observed in these seeds with embryo.

After plants originating in auxin treatment grew in the suitable size for sampling (1 to 2 months after germination), DNA contents of these plants originating in auxin treatment were measured by flow cytometry, then chromosomes were observed simultaneously and the number of chromosomes was investigated.

Figure 2:
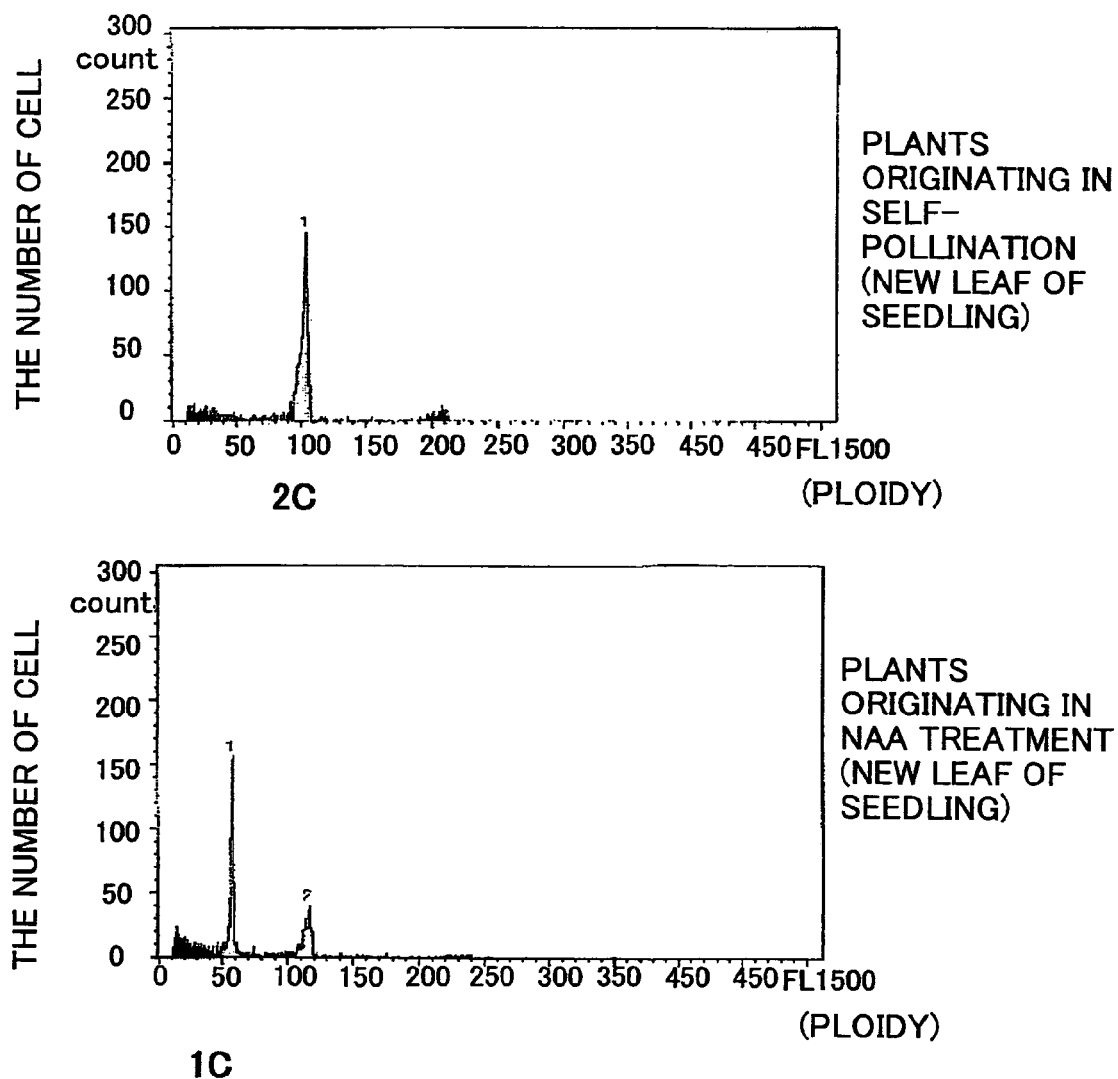
FIG. 2 is views showing results of analysis based on flow cytometry.
Figure 3:
FIG. 3 is views showing observation results of chromosomes under a microscope.
Figure 3:

The investigation was done by obtaining new leaf of seedling, plants treated with α-naphthaleneacetic acid (NAA) of the present invention were investigated and also plants originating in self-pollination were investigated as a comparison. FIG. 2 is views showing results of analysis based on flow cytometry. FIG. 3 is views showing observation results of chromosomes under a microscope. As can be seen in FIG. 2, in the investigation for DNA amounts using flow cytometry equipment, a peak of the plant originating in auxin treatment was observed at position of half ploidy level of a peak seen with the plant originating in self-pollination.

In the observation of chromosomes, as can be seen in FIG. 3, it was observed that the number of chromosomes of the plant originating in auxin treatment was 16, and it was found that this is half of the number of chromosomes, 32 chromosomes for Bletilla Bringantes.

5 to 6 months after germination, when DNA contents of plants originating in auxin treatment was measured again with flow cytometry equipment, its peak is observed at the almost same position of a peak of plants originating in self-pollination. Thus, it should be recognized that the number of chromosomes of plants originating in auxin treatment was doubled naturally 2 to 5 months after germination.

From these results of observations, it is recognized that plants originating in auxin treatment are haploid. It is also recognized that the number of chromosomes of plants originating in auxin treatment becomes doubled naturally as time goes by after auxin treatment, and that it is required to affirm the number of chromosomes within two months after germination.

As already mentioned above, the growing orchid haploid of the present invention is able to provide a pure line plant which is required in constructing a seed propagation variety of orchid, thereby, a supply of stable superior breed with low risks like mutations becomes possible for a long period of time.

The present invention is not limited to the specifically disclosed embodiments, and variations and modifications may be made without departing from the scope of the present invention.

The present application is based on Japanese priority application No. 2002-213746 filed on Jul. 23, 2002, the entire contents of which are hereby incorporated by reference.

What is claimed is:

1. A method of constructing orchid haploid, comprising
   dropping an auxin solution to unfertilized orchid flowers;
   forming seeds based on parthenogenesis, germinating and growing the seed; and
   obtaining an orchid haploid.

2. The method of constructing orchid haploid of claim 1, wherein said dropping of said auxin solution to unfertilized orchid flowers is treated within 30 days after blooming.

3. The method of constructing orchid haploid of claim 1, wherein said auxin solution is dropped to a column or a part including said column of unfertilized orchid flowers.

4. The method of constructing orchid haploid of claim 1, wherein a concentration of said auxin solution is between 0.1 and 5.0%.

5. The method of constructing orchid haploid of claim 1, wherein said auxin solution is selected from a group consisting of Indoleacetic acid (IAA), 4-chloro-indoleacetic acid, phenylacetic acid, 2,4-dichloro-phenoxyacetic acid (2,4-D), α-naphthaleneacetic acid (NAA), 2,6-dichloro-benzoic acid, indolebutyric acid (IBA), 4-chloro-phenoxyacetic acid, 5-chloro-indazole ethyl acetate and 2,4,5-trichloro-phenylacetic acid.

6. A method of constructing a seed propagation variety of orchid comprising:
   dropping an auxin solution to unfertilized orchid flowers;
   forming seeds based on parthenogenesis;
   germinating the seeds;
   judging plants grown from the germinated seeds for being haploid;
   selecting the judged haploid plants; and
   growing the haploid plants.

7. The method of constructing a seed propagation variety of orchid comprising:
   dropping an auxin solution to unfertilized orchid flowers;
   forming seeds based on parthenogenesis;
   germinating the seeds;
   judging plants grown from the germinated seeds for being haploid;
   selecting the judged haploid plants; and
   growing the haploid plants,
   wherein said judgment as haploid plants are done by measuring DNA contents or the number of chromosomes of samples obtained within a period between one to five months after germination.

* * * * *